US009487640B2

(12) United States Patent
Kwon et al.

(10) Patent No.: US 9,487,640 B2
(45) Date of Patent: Nov. 8, 2016

(54) PLASTICIZERS FOR RESIN COMPOSITIONS AND RESIN COMPOSITIONS INCLUDING THE SAME

(75) Inventors: Tae Wook Kwon, Daejeon (KR); Soo Young Hwang, Daejeon (KR); Jin Su Ham, Daejeon (KR); Ki Nam Chung, Daejeon (KR); Jong Ho Lim, Daejeon (KR); Sung Gi Lee, Daejeon (KR)

(73) Assignees: SK INNOVATION CO., LTD., Seoul (KR); SK GLOBAL CHEMICAL CO., LTD., Seoul (KR)

( * ) Notice: Subject to any disclaimer, the term of this patent is extended or adjusted under 35 U.S.C. 154(b) by 332 days.

(21) Appl. No.: 14/118,374

(22) PCT Filed: May 17, 2012

(86) PCT No.: PCT/KR2012/003893
§ 371 (c)(1),
(2), (4) Date: Nov. 18, 2013

(87) PCT Pub. No.: WO2012/157974
PCT Pub. Date: Nov. 22, 2012

(65) Prior Publication Data
US 2014/0107271 A1  Apr. 17, 2014

(30) Foreign Application Priority Data

May 19, 2011  (KR) ........................ 10-2011-0047126
May 7, 2012   (KR) ........................ 10-2012-0048260

(51) Int. Cl.
| | | |
|---|---|---|
| *A61L 15/62* | (2006.01) | |
| *C08K 5/06* | (2006.01) | |
| *C08K 5/00* | (2006.01) | |
| *C07C 69/14* | (2006.01) | |
| *C07C 43/11* | (2006.01) | |
| *C07C 43/178* | (2006.01) | |
| *C08K 5/10* | (2006.01) | |
| *C08L 27/06* | (2006.01) | |
| *C08L 63/00* | (2006.01) | |
| *C08L 69/00* | (2006.01) | |
| *C08L 75/04* | (2006.01) | |

(52) U.S. Cl.
CPC ................ *C08K 5/06* (2013.01); *C07C 43/11* (2013.01); *C07C 43/1785* (2013.01); *C07C 69/14* (2013.01); *C08K 5/0016* (2013.01); *C08K 5/10* (2013.01); *C08L 27/06* (2013.01); *C08L 63/00* (2013.01); *C08L 69/00* (2013.01); *C08L 75/04* (2013.01); *C08L 2201/06* (2013.01)

(58) Field of Classification Search
CPC ............ C08K 5/06; C08K 5/09; C08K 5/10; C08K 5/0016; C08L 27/00; C08L 63/00; C08L 69/00; C08L 75/00; C08L 101/16
USPC .......................................................... 524/306
See application file for complete search history.

(56) References Cited

U.S. PATENT DOCUMENTS

| | | | | |
|---|---|---|---|---|
| 3,186,961 A * | 6/1965 | Sears | ................... | C08K 5/0016 524/111 |
| 4,500,704 A * | 2/1985 | Kruper, Jr. | ............. | C08G 64/34 528/370 |
| 4,795,771 A | 1/1989 | Yoshihara | | |
| 4,952,645 A * | 8/1990 | Mulhaupt | ............ | C08G 59/145 525/438 |
| 5,187,218 A * | 2/1993 | Masumoto | .............. | C08L 59/00 524/306 |
| 5,417,870 A * | 5/1995 | Andrei | .................. | H01M 6/181 252/571 |
| 5,936,014 A * | 8/1999 | Voigt | ........................ | C08L 3/06 524/51 |
| 6,391,069 B1 * | 5/2002 | Gozdz | ................. | B29C 65/4895 29/623.3 |
| 6,752,964 B1 * | 6/2004 | Grubbs | ................ | G01N 27/126 204/412 |
| 6,783,897 B2 * | 8/2004 | Kang | ..................... | C08F 230/08 429/313 |
| 2004/0242803 A1* | 12/2004 | Ohme | ..................... | C08L 67/04 525/400 |
| 2005/0154148 A1* | 7/2005 | Nakamichi | ............. | C08L 67/04 525/450 |
| 2007/0027240 A1 | 2/2007 | Lee et al. | | |
| 2011/0054089 A1 | 3/2011 | Kishimoto et al. | | |
| 2011/0195148 A1* | 8/2011 | Mentink | ........... | C08G 18/6484 426/3 |
| 2012/0157637 A1* | 6/2012 | Park | ....................... | C09J 169/00 525/461 |
| 2012/0220680 A1* | 8/2012 | Bastioli | ................ | C08G 63/183 521/182 |
| 2012/0316256 A1 | 12/2012 | Rashid et al. | | |

FOREIGN PATENT DOCUMENTS

| | | | | | |
|---|---|---|---|---|---|
| GB | 1470202 A | * | 4/1977 | ......... | C08G 65/3322 |
| JP | 06172582 A | * | 6/1994 | ............... | C08K 5/06 |
| JP | 2004-337299 | | 12/2004 | | |
| JP | 2006-022268 | | 1/2006 | | |
| KR | 10-2007-0082421 | | 8/2007 | | |
| KR | 10-2007-0092490 | | 9/2007 | | |
| WO | 2011/051689 A2 | | 5/2011 | | |

OTHER PUBLICATIONS

JP 06172582A Tsubaki, Jun. 1994; Machine translation.*

(Continued)

Primary Examiner — Jane L Stanley
(74) Attorney, Agent, or Firm — Hauptman Ham, LLP

(57) ABSTRACT

Provided are a plasticizer for a resin composition including any one or more selected from a polyvinyl chloride resin, a polyurethane resin, an epoxy resin, a polycarbonate resin or a biodegradable resin, which has excellent mechanical properties such as tensile strength, elongation and hardness, and shape processability, and particularly has excellent flexibility at low temperatures, does not cause bleeding because compatibility with the resins is good, and has excellent transparency, heat resistance, cold resistance and durability, and a resin composition including the same.

6 Claims, No Drawings

(56) References Cited

OTHER PUBLICATIONS

Shi Wancong et al, Chemical Industrial Press, 2002, <http://www.cip.com.cn>.

Li Zhenxi, "Synthesis and Application of Selexol and its Market Analysis", Guizhou Chemical Industry, China Academic Journal Electronic Publishing House, Apr. 2003, <www.cnki.net>.
European Search Report for corresponding European Application No. 12786049.2, dated Jan. 7, 2015.

* cited by examiner

PLASTICIZERS FOR RESIN COMPOSITIONS AND RESIN COMPOSITIONS INCLUDING THE SAME

TECHNICAL FIELD

The present invention relates to a plasticizer of any one or more resins selected from polyvinyl chloride, epoxy, polyurethane, and aliphatic or aromatic polycarbonate resins and a biodegradable resin, and a resin composition including the same.

BACKGROUND ART

General resins such as polyethylene (PE), polypropylene (PP), polyurethane (PU), polyvinyl chloride (PVC) and polycarbonate (PC) are used in various industrial fields such as living things, home appliances, cloths, vehicles, construction and packing materials because of excellent physical properties thereof.

Among them, polycarbonate is generally aromatic polycarbonate using bis-phenol A, but the use of aliphatic polycarbonate for improving physical properties of aromatics is apt to increase. Particularly, examples of aliphatic polycarbonate receiving attention as environmentally-friendly polycarbonate include polypropylene carbonate manufactured by copolymerization of propylene oxide (PO) and carbon dioxide and polyethylene carbonate manufactured by copolymerization of ethylene oxide (EO) and carbon dioxide through a similar reaction path, and in order to improve mechanical properties thereof, a terpolymer additionally using cyclohexen oxide, glycidyl ethers, glycidyl esters or the like in addition to propylene oxide and ethylene oxide has been developed and applied.

The polyvinyl chloride resin, the polyurethane resin, the epoxy resin or the polycarbonate resin may provide various processing physical properties by appropriately adding various additives such as a plasticizer, a stabilizer, a viscosity controlling agent, an internal release agent and a pigment, and the plasticizer among the additives is an essential additive added to the resins to provide various physical properties and performances such as processability, flexibility and adhesive property.

Volatility of the plasticizer should be very low, and performance of the plasticizer is continuously shown while a plastic composition is shaped by using the resins and the shaped products are used in practice, such that the plasticizer is very important in view of maintenance of physical properties. Further, the plasticizer provided to be applied to food and medical fields and the purpose of contact with human body should be harmless in view of health, and in the case of interior materials for construction, discharging of a volatile organic compound should be delayed.

Until now, examples of the plasticizer used for this purpose may include dialkyl phthalates, and particularly, it is known that dibasic esters such as ester compounds of citric acids or dioctyl adipates may be used as polycarbonates. However, it is expected that use of dialkyl phthalate will be significantly reduced because there is a controversy over regenerated toxicity under the law regulating toxic materials regarding stability of human body, and particularly, in the case of polypropylene carbonate or a copolymer of polyethylene carbonate and glycidyl ether or glycidyl ester thereof, since plasticity of the plasticizer such as dialkyl phthalate or dibasic esters is not sufficient, when the content of the plasticizer is low, such as, 10% or less, it is difficult to sufficiently reduce a glass transition temperature, and the use content should be high in order to ensure sufficient flexibility, but in this case, there is a problem in that surface stickiness after the resin composition is processed is increased. Further, since physical properties such as mechanical properties, flexibility at low temperatures, compatibility and durability of the plasticizer need to be improved, there is an urgent demand for developing a plasticizer improving this.

DISCLOSURE

Technical Problem

An object of the present invention is to provide a plasticizer for a resin composition including any one or more selected from a polyvinyl chloride resin, a polyurethane resin, an epoxy resin, a polycarbonate resin or a biodegradable resin, which has excellent mechanical properties such as tensile strength, elongation and hardness, and shape processability, and particularly has excellent flexibility at low temperatures, does not cause bleeding because compatibility with the resins is good, and has excellent transparency, heat resistance, cold resistance and durability, and a resin composition including the same.

Technical Solution

In one general aspect, a resin composition includes any one or more resins selected from a polyvinyl chloride resin, a polyurethane resin, a polycarbonate resin, an epoxy resin or a biodegradable resin, and a plasticizer represented by the following Formula 1.

[Formula 1]

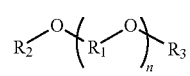

($R_1$ is straight- or side-chained (C1-C8)alkylene, (C5-C10)cycloaliphatic alkylene or (C6-C12)arylene, $R_2$ and $R_3$ are each independently a straight- or side-chained (C1-C18) alkyl group, a (C5-C10)cycloaliphatic alkyl group, a (C6-C12)aryl group or the following Formula 2 or Formula 3, and n is 1 to 50)

[Formula 2]

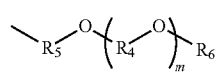

[Formula 3]

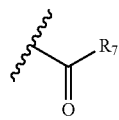

($R_4$ and $R_5$ are straight- or side-chained (C1-C8)alkylene, (C5-C10)cycloaliphatic alkylene or (C6-C12)arylene, $R_6$ is a straight- or side-chained (C1-C18)alkyl group, a (C5-C10) cycloaliphatic alkyl group, or a (C6-C12)aryl group, m is 1 to 50, and $R_7$ is a straight- or side-chained (C1-C18)alkyl group, a (C5-C10)cycloaliphatic alkyl group or a (C6-C12) aryl group).

The plasticizer includes a compound represented by the following Formula 4 or Formula 5.

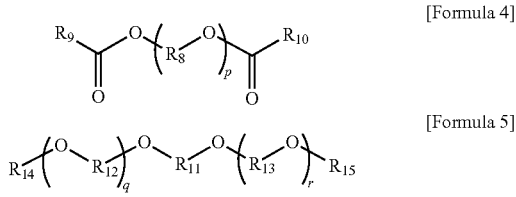
[Formula 4]

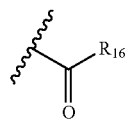
[Formula 5]

($R_8$ is straight- or side-chained (C1-C8)alkylene, (C5-C10)cycloaliphatic alkylene or (C6-C12)arylene, $R_9$ and $R_{10}$ are each independently a straight- or side-chained (C1-C18) alkyl group, a (C5-C10)cycloaliphatic alkyl group or a (C6-C12)aryl group, $R_{11}$, $R_{12}$ and $R_{13}$ are straight- or side-chained (C1-C8)alkylene, (C5-C10)cycloaliphatic alkylene or (C6-C12)arylene, $R_{14}$ and $R_{15}$ are each independently a straight- or side-chained (C1-C18)alkyl group, a (C5-C10) cycloaliphatic alkyl group, a (C6-C12)aryl group or the following Formula 6, and p, q and r are 1 to 40)

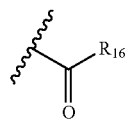
[Formula 6]

($R_{16}$ is a straight- or side-chained (C1-C18)alkyl group, a (C5-C10)cycloaliphatic alkyl group or a (C6-C12)aryl group).

The resin composition according to an exemplary embodiment of the present invention may include 1 to 70 parts by weight of the plasticizer based on 100 parts by weight of the resin.

Polycarbonate according to the exemplary embodiment of the present invention may be a matter where polypropylene carbonate or polyethylene carbonate and alkylene oxide are copolymerized.

In this case, alkylene oxide may be selected from cyclohexene oxide, glycidyl ester, glycidylether or butylene oxide.

A weight average molecular weight of polycarbonate according to the exemplary embodiment of the present invention may be 2,000 to 3,000,000 g/mol.

A specific gravity of polycarbonate according to the exemplary embodiment of the present invention may be 1.0 to 1.3.

The biodegradable resin according to the exemplary embodiment of the present invention may be any one or more selected from aliphatic polyester, polycaprolactone, polylactic acid, polybutylene succinate or polyvinyl alcohol.

In another general aspect, a plasticizer for a resin composition is represented by the following Formula 1.

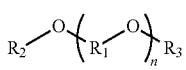
[Formula 1]

($R_1$ is straight- or side-chained (C1-C8)alkylene, (C5-C10)cycloaliphatic alkylene or (C6-C12)arylene, $R_2$ and $R_3$ are each independently a straight- or side-chained (C1-C18) alkyl group, a (C5-C10)cycloaliphatic alkyl group, a (C6-C12)aryl group or the following Formula 2 or Formula 3, and n is 1 to 50)

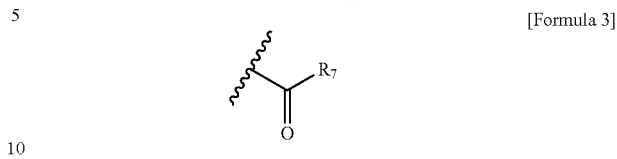
[Formula 2]

[Formula 3]

($R_4$ and $R_5$ are straight- or side-chained (C1-C8)alkylene, (C5-C10)cycloaliphatic alkylene or (C6-C12)arylene, $R_6$ is a straight- or side-chained (C1-C18)alkyl group, a (C5-C10) cycloaliphatic alkyl group, or a (C6-C12)aryl group, m is 1 to 50, and $R_7$ is a straight- or side-chained (C1-C18)alkyl group, a (C5-C10)cycloaliphatic alkyl group or a (C6-C12) aryl group).

The plasticizer according to the exemplary embodiment of the present invention includes a compound represented by the following Formula 4 or Formula 5.

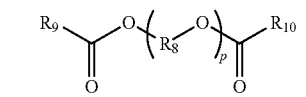
[Formula 4]

[Formula 5]

($R_8$ is straight- or side-chained (C1-C8)alkylene, (C5-C10)cycloaliphatic alkylene or (C6-C12)arylene, $R_9$ and $R_{10}$ are each independently a straight- or side-chained (C1-C18) alkyl group, a (C5-C10)cycloaliphatic alkyl group or a (C6-C12)aryl group, $R_{11}$, $R_{12}$ and $R_{13}$ are straight- or side-chained (C1-C8)alkylene, (C5-C10)cycloaliphatic alkylene or (C6-C12)arylene, $R_{14}$ and $R_{15}$ are each independently a straight- or side-chained (C1-C18)alkyl group, a (C5-C10) cycloaliphatic alkyl group, a (C6-C12)aryl group or the following Formula 6, and p, q and r are 1 to 40)

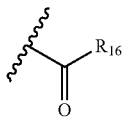
[Formula 6]

($R_{16}$ is a straight- or side-chained (C1-C18)alkyl group, a (C5-C10)cycloaliphatic alkyl group or a (C6-C12)aryl group).

The resin according to the exemplary embodiment of the present invention may include any one or more selected from a polyvinyl chloride resin, a polyurethane resin, a polycarbonate resin, an epoxy resin or a biodegradable resin.

Advantageous Effects

As described above, a plasticizer for a resin composition according to the present invention has very excellent tensile strength and a low glass transition temperature, such that there are advantages in that shaping into a film is excellent, flexibility may be maintained at low temperatures so as to be applied to processing of flexible products such as films or artificial leather sheet, bleeding does not occur because compatibility with the resins is good, and a life-span of products such as films and sheets manufactured by using the resin composition may be extended because transparency, heat resistance and cold resistance are excellent.

BEST MODE

Hereinafter, a plasticizer for a resin composition of the present invention, and a resin composition using the same will be described in detail. The terminologies including technical terms and scientific terms used in the present invention have the same meanings that those skilled in the art generally understand, if not defined, and the detailed description of a related known function or configuration that may make the purpose of the present invention unnecessarily ambiguous in describing the present invention will be omitted in the following description and accompanying drawings.

The plasticizer for the resin composition according to the present invention is represented by the following Formula 1.

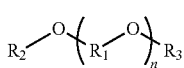

[Formula 1]

$R_1$ is straight- or side-chained (C1-C8)alkylene, (C5-C10)cycloaliphatic alkylene or (C6-C12)arylene, $R_2$ and $R_3$ are each independently a straight- or side-chained (C1-C18) alkyl group, a (C5-C10)cycloaliphatic alkyl group, a (C6-C12)aryl group or the following Formula 2 or Formula 3, and n is 1 to 50.

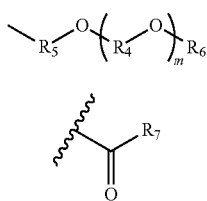

[Formula 2]

[Formula 3]

$R_4$ and $R_5$ are straight- or side-chained (C1-C8)alkylene, (C5-C10)cycloaliphatic alkylene or (C6-C12)arylene, $R_6$ is a straight- or side-chained (C1-C18)alkyl group, a (C5-C10)cycloaliphatic alkyl group, or a (C6-C12)aryl group, m is 1 to 50, and $R_7$ is a straight- or side-chained (C1-C18)alkyl group, a (C5-C10)cycloaliphatic alkyl group or a (C6-C12) aryl group.

$R_1$ may be preferably methylene, ethylene, n-propylene, i-propylene, n-butylene, i-butylene, n-pentylene, i-pentylene, n-hexylene, i-hexylene, n-heptylene or i-heptylene, and more preferably selected from —$CH_2CH_2$—, —$CH_2CH_2CH_2$—, —$CH_2CH(CH_3)$—, —$CH(CH_3)CH_2$—, —$CH_2CH_2CH_2CH_2$—, —$CH(CH_3)CH_2CH_2$—, —$CH_2CH(CH_3)CH_2$—, —$CH_2CH_2CH_2CH_2CH_2$—, —$CH(CH_3)CH_2CH_2CH_2$—, $CH_2CH(CH_3)CH_2CH_2$—, —$CH_2CH_2CH_2CH_2CH_2CH_2$—, —$CH(CH_3)CH_2CH_2CH_2CH_2$—, —$CH_2CH(CH_3)CH_2CH_2CH_2$—, —$CH_2CH(CH_3)CH_2CH_2CH_2$— or —$CH_2CH_2CH(CH_3)CH_2CH_2$—.

The plasticizer according to the exemplary embodiment of the present invention includes a compound represented by the following Formula 4 or Formula 5.

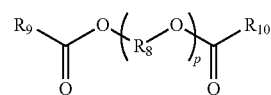

[Formula 4]

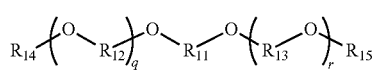

[Formula 5]

$R_8$ is straight- or side-chained (C1-C8)alkylene, (C5-C10)cycloaliphatic alkylene or (C6-C12)arylene, $R_9$ and $R_{10}$ are each independently a straight- or side-chained (C1-C18) alkyl group, a (C5-C10)cycloaliphatic alkyl group or a (C6-C12)aryl group, $R_{11}$, $R_{12}$ and $R_{13}$ are straight- or side-chained (C1-C8)alkylene, (C5-C10)cycloaliphatic alkylene or (C6-C12)arylene, R14 and R15 are each independently a straight- or side-chained (C1-C18)alkyl group, a (C5-C10) cycloaliphatic alkyl group, a (C6-C12)aryl group or the following Formula 6, and p, q and r are 1 to 40.

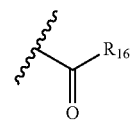

[Formula 6]

$R_{16}$ is a straight- or side-chained (C1-C18)alkyl group, a (C5-C10)cycloaliphatic alkyl group or a (C6-C12)aryl group.

The plasticizer for the resin composition according to the exemplary embodiment of the present invention includes the following Formula 7 or Formula 8.

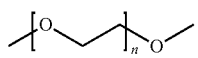

[Formula 7]

($n \approx 10$)

$^1$H-NMR(CDCl$_3$, 500 MHz) : δ 3.38(6H,s), 3.52~3.56 (4H,m), 3.64~3.66(36H,m)

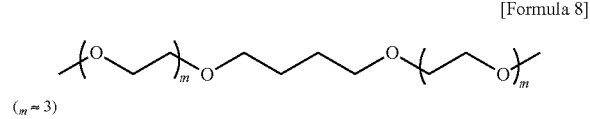

[Formula 8]

($m \approx 3$)

$^1$H-NMR(CDCl$_3$, 500 MHz) : δ 1.63(4H,tt), 3.38(6H,s), 3.65(4H,t), 3.53~3.59(8H,m), 3.63~3.67(16H,m)

The present invention may manufacture a resin composition by adding the plasticizer represented by Formula 1 to any one or more resins selected from a polyvinyl chloride resin, a polyurethane resin, an epoxy resin, a polycarbonate resin or a biodegradable resin. In this case, it is preferable that the addition amount of the plasticizer added to the resin be 1 to 70 parts by weight based on 100 parts by weight of the resin.

The composition including the plasticizer according to the present invention may appropriately increase or decrease the plasticizer according to the purpose of the resin composition, but in the case where it is added in an amount of less than 1 part by weight, flexibility or processability that may be implemented by the plasticizer cannot be accomplished, and in the case where it is added in an amount of more than 70 parts by weight, it is difficult to ensure an appropriate mechanical property, viscosity is excessively reduced, and a bleeding phenomenon may occur, which are not preferable.

The plasticizer according to the present invention is mixed with any one or more resins selected from a polyvinyl chloride resin, a polyurethane resin, an epoxy resin, a polycarbonate resin or a biodegradable resin to form the resin composition, but the resin is not limited thereto, but may be applied to resins selected from a chlorine-containing resin selected from chlorinated polyvinyl chloride, polyvinylidene chloride, chlorinated polyethylene, vinyl chloride-vinyl acetate copolymer, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-various vinyl ether copolymer and the like, mutual blend forms thereof, and blend forms, block copolymers and graft copolymers of the chlorine-containing resin and a chlorine-free synthetic resin, for example, acrylonitrile-styrene copolymer, acrylonitrile-styrene-butadiene tercopolymer, ethylene-vinyl acetate copolymer, polyester and the like. Further, it may be applied to the biodegradable resin, for example, aliphatic polyester, polycaprolactone, polybutylene succinate, polylactic acid (PLA), polyvinyl alcohol or the like, but is not limited thereto.

The polyvinyl chloride resin composition including the plasticizer according to the present invention may be manufactured by the method known well in the art, for example, the case where curing is performed after being added to the resin where the molecular weight is sufficiently increased through crosslinking or curing in advance or to an oligomer type precursor and the like are known.

The epoxy resin composition including the plasticizer of the present invention may be manufactured by the method known well in the art, and particularly, it is most preferable to add the plasticizer before a curing reaction occurs by a curing agent.

The polycarbonate resin composition including the plasticizer of the present invention may be manufactured by the method known well in the art.

It is preferable to use polyalkylene carbonate as the polycarbonate resin. In this case, alkylene includes ethylene, propylene, 1-butylene, cyclohexeneoxide, alkylglycidylether, n-butyl, n-octyl or the like, but is not limited thereto. It is preferable to use polyalkylene carbonate having the weight average molecular weight of 2,000 to 3,000,000 g/mol.

Polypropylene carbonate or polyethylene carbonate may be used as a specific example of polyalkylene carbonate, or a copolymer having a weight average molecular weight of 2,000 to 3,000,000 g/mol may be used as polycarbonate copolymerized with alkylene oxide. In this case, specific examples of alkylene oxide include cyclohexene oxide, glycidyl ester, glycidylether, butylene oxide and the like.

Bisphenol A, polycarbonate derived from hydrogenated bisphenol A or a copolymer thereof may be used as the polycarbonate resin.

The specific gravity of polyalkylene carbonate is 1.0 to 1.3. If the specific gravity deviates from the aforementioned range, the plasticizer is not well mixed with the polyalkylene carbonate resin but separated therefrom, such that it is difficult to ensure the effect of the plasticizer in the resin composition.

The polyurethane resin composition including the plasticizer of the present invention may be manufactured by the method known well in the art.

As described above, the resin composition according to the present invention exhibits an improvement in excellent physical properties of hardness, tensile strength, elongation, elastic modulus, bleeding and glass transition temperature. Specifically, the resin composition of the present invention has hardness (Shore A) of 37 to 56 A, tensile strength of 120 to 130 Kgf/cm$^2$, elongation of 405 to 495%, modulus of 28 to 36 Kgf/cm$^2$ and glass transition temperature (Tg) that is lower than that of a resin composition to which a known plasticizer is added, and bleeding did not occur. As described above, since the resin composition including the plasticizer of the present invention exhibits excellent physical properties because of excellent plasticizing efficiency, it is expected that it is possible to manufacture products having more excellent physical properties in a known resin composition or products using the same in various fields.

By manufacturing plastics using the resin composition including the plasticizer, tensile strength is excellent, shaping into the film is excellent because the glass transition temperature is low, and flexibility is maintained at low temperatures to allow processing into flexible products such as films or artificial leather sheets to be feasible, bleeding does not occur and an extraction property by an organic solvent or water is reduced because compatibility with the resins is excellent, and a life-span of products such as films and sheets manufactured by using the resin composition may be extended.

The resin composition including the plasticizer of the present invention may be used in construction materials such as wall finishing materials, flooring materials, window frames and wallpapers; wire covering materials; interior and exterior materials for vehicles; agricultural materials such as houses and tunnels; packing materials of foods such as fishes, such as wraps and trays; coat forming agents such as underbody silants, plastisol, paints and ink; and miscellaneous goods such as synthetic leather, coated fabrics, hoses, pipes, sheets, toys for infants and gloves, but they are just examples and not limited. Hereinafter, constitutions and effects of the present invention will be described in more detail with reference to the specific Examples and Comparative Examples. These embodiments may, however, should not be construed as being limited to the embodiments set forth herein, but are provided such that this disclosure will be thorough and more clearly understood. In Examples and Comparative Examples, physical properties were evaluated by the following methods.

Hardness

The hardness value was read 5 sec after the needle of the hardness tester (A Type) was completely unloaded onto one point of the sample based on the ASTM D2240 method, and after three points were tested with respect to each sample, the average value thereof was taken. It was used as an index exhibiting plasticizing efficiency.

Tensile Strength, Elongation, Modulus at 100% Elongation

The measurement was performed by using UTM based on the ASTM D412 method. After the sample having the dumbbell shape was pulled at the crosshead speed of 200 mm/min, the point at which the sample was broken was measured. Modulus at 100% elongation is tensile strength at 100% elongation and has a high relationship with compatibility with the resin of the plasticizer.

Bleeding

Whether the plasticizer flowed out of the surface was confirmed by applying pressure of 0.01 kg/cm2 at 35° C. This method has a relationship with compatibility with the plasticizer and the resin.

Glass Transition Temperature

Tg was measured by using DSC in the range of −30 to 100° C. Tg has a high relationship with compatibility with the plasticizer.

EXAMPLE 1

Polyethylene glycol (PEG (n=4), number average molecular weight 200, and Sigma-Aldrich, Co., Ltd.), methyl iodide, and potassium hydroxide were put into THF at the ratio of 1:2.1:4, and agitated at normal temperature for 2 hours. The solvent was distilled under the reduced pressure, water was added, and extraction was performed by using dichloromethane. After the collected organic layer was dried by magnesium sulfate ($MgSO_4$), methoxy capped PEG (n=4) was obtained at the yield of 60% by vaporizing the solvent. $^1$H-NMR($CDCl_3$, 500 MHz) : δ 3.38(6H,s), 3.54~3.64(16H,m)

EXAMPLE 2

The plasticizer was manufactured under the same condition as Example 1, except that polyethylene glycol (PEG (n=8), number average molecular weight 400, and Sigma-Aldrich, Co., Ltd.) was used instead of PEG (n=4). $^1$H-NMR ($CDCl_3$, 500 MHz) : δ 3.38(6H,s), 3.54~3.64(32H,m)

EXAMPLE 3

The plasticizer was manufactured under the same condition as Example 1, except that PEG (n=4) was changed to polypropylene glycol (PPG (n=8), average molecular weight 425, and Sigma-Aldrich, Co., Ltd.). $^1$H-NMR($CDCl_3$, 500 MHz) : δ 1.37(24H,d), 3.34(6H,s), 3.40~3.68(24H,m)

EXAMPLE 4

After PEG (n=8) and dichloromethane were put into the round bottom flask, acetic anhydride, triethylamine, and dimethylamino pyridine were added at the ratio of 2:2:0.1 based on PEG, and agitated at normal temperature for 5 hours. If the reaction was finished, after the organic layer was washed with water using a separatory funnel, the solvent was vaporized, the organic layer passed through the silica bed. After the remaining solvent was further removed, acetylated PEG (n=8) was obtained at the yield of 56%. $^1$H-NMR($CDCl_3$, 500 MHz) : δ 2.20(6H,s), 3.62(24H,m), 3.68(4H,m), 4.24(4H,m)

EXAMPLE 5

The plasticizer was manufactured under the same condition as Example 4, except that PEG (n=8) was changed into PPG (n=8). $^1$H-NMR($CDCl_3$, 500 MHz) : δ 1.37(24H,d), 2.20(6H,s), 3.34~4.32(32H,m)

EXAMPLE 6

1 mol poly(ethylene glycol)monomethyl ether (n=10, hereinafter, mPEG), average molecular weight 500, and Sigma-Aldrich, Co., Ltd.), 50 ml of benzene, and 60 ml of sodium hydroxide (NaOH, 50%) were injected into the round bottom flask. Benzyl chloride and tetrabutylammonium hydrogen sulfate were added at the ratio of 1.1:0.05 based on mPEG, and then agitated at 80° C. for 3 hours. If the reaction was finished, after the organic layer was washed with water by using the separatory funnel, the solvent was vaporized, and 70% poly(ethylene glycol)benzyl methyl ether (n=10) was obtained at the yield of 75% through distillation. $^1$H-NMR($CDCl_3$, 500 MHz) : δ 3.38(3H,s), 3.52~3.56(4H,s), 3.64~3.66(36H,m), 7.00~7.40(5H,m)

EXAMPLE 7

16 g of triethylene glycol monomethyl ether (Sigma-Aldrich, Co., Ltd., purity 95%) and 8.5 g of potassium hydroxide were put into 250 ml of tetrahydrofuran (THF) in the round flask, and agitated for 30 min. 10 ml of 1,4-dibromobutane (Sigma-Aldrich, Co., Ltd., purity 99%) was slowly applied in drops by using the dropping funnel. After finishing of the reaction was confirmed by GC, the organic layer was washed with water by using the separatory funnel, the solvent was vaporized, and the product having purity of 99.5% was obtained through distillation of the reaction product. $^1$H-NMR($CDCl_3$, 500 MHz) : δ 1.63(4H,m), 3.38 (6H,s), 3.65(4H,t), 3.53~3.59(8H,m), 3.63~3.67(16H,m)

EXAMPLE 8

16 g of triethylene glycol monomethyl ether (Sigma-Aldrich, Co., Ltd., purity 95%) and 8.5 g of potassium hydroxide were put into 250 ml of tetrahydrofuran (THF) in the round flask, and agitated for 30 min. 12 ml of 1,5-dibromopentane (Sigma-Aldrich, Co., Ltd., purity 97%) was slowly applied in drops by using the dropping funnel. After finishing of the reaction was confirmed by GC, the organic layer was washed with water by using the separatory funnel, the solvent was vaporized, and the product having purity of 99.5% was obtained through distillation of the reaction product. $^1$H-NMR($CDCl_3$, 500 MHz) : δ 1.63(4H,m), 1.71 (2H,m) 3.38(6H,s), 3.65(4H,t), 3.53~3.59(8H,m), 3.63~3.67 (16H,m)

EXAMPLE 9

16 g of triethylene glycol monomethyl ether (Sigma-Aldrich, Co., Ltd., purity 95%) and 8.5 g of potassium hydroxide were put into 250 ml of tetrahydrofuran (THF) in the round flask, and agitated for 30 min. 15 ml of 1,6-dibromopentane (Sigma-Aldrich, Co., Ltd., purity 96%) was slowly applied in drops by using the dropping funnel. After finishing of the reaction was confirmed by GC, the organic layer was washed with water by using the separatory funnel, the solvent was vaporized, and the product having purity of 99% was obtained through distillation of the reaction product. $^1$H-NMR($CDCl_3$, 500 MHz) : δ 1.52(4H,m), 1.63(4H, m), 3.38(6H,s), 3.65(4H,t), 3.53~3.59(8H,m), 3.63~3.67 (16H,m)

EXAMPLE 10

30 g of 3,6,9,14,17,20-hexaoxa-docosane-1,22-diol (BDO-EO6, Hannong Chemicals, Inc.) having the number average molecular weight of 350 and 15 g of potassium hydroxide were put into 250 ml of tetrahydrofuran (THF) in the round flask, and agitated for 1 hour. After agitation for 1 hour, 30 g of methyl iodide was added, and agitation was further performed for 3 hours. After finishing of the reaction was confirmed by GC, the organic layer was washed with water by using the separatory funnel, the product was filtered and dried with MgSO4, and the solvent was removed. The following Table 1 is a table exhibiting a molecular weight distribution according to the EO reaction mol number analyzed by using GC.

TABLE 1

| Retention time (Ret. Time) | wt % | Molecular weight | EO reaction Mol number |
|---|---|---|---|
| 11.96 | 0.8 | 162 | 1 |
| 15.86 | 4.1 | 206 | 2 |
| 19.07 | 8.3 | 250 | 3 |
| 21.84 | 12.0 | 294 | 4 |
| 24.27 | 15.0 | 338 | 5 |
| 26.43 | 15.2 | 382 | 6 |
| 28.38 | 13.7 | 426 | 7 |
| 30.14 | 10.9 | 470 | 8 |
| 31.85 | 8.0 | 514 | 9 |
| 34.19 | 5.2 | 558 | 10 |
| 37.85 | 3.2 | 602 | 11 |
| 43.79 | 1.9 | 646 | 12 |
| 53.59 | 1.1 | 690 | 13 |

EXAMPLE 11

22 g of dipropylene glycol monomethyl ether (Sigma-Aldrich, Co., Ltd., purity 99%) and 11 g of potassium hydroxide were put into 250 ml of tetrahydrofuran (THF) in the round flask, and agitated for 30 min, and 15 ml of 1,4-dibromobutane (Sigma-Aldrich, Co., Ltd., purity 99%) was slowly applied in drops by using the dropping funnel. After the application was finished, the temperature was increased to perform the reaction under THF reflux. After finishing of the reaction was confirmed by GC, the organic layer was washed with water by using the separatory funnel, the solvent was vaporized, and the product having purity of 99.0% was obtained through distillation of the reaction product. $^1$H-NMR(CDCl$_3$, 500 MHz) : δ 1.37(12H,d), 1.59 (4H,m), 3.38 (6H,s), 3.40~3.68(16H,m)

EXAMPLE 12

20 g of tripropylene glycol monomethyl ether (Sigma-Aldrich, Co., Ltd., purity 97.5%) and 7 g of potassium hydroxide were put into 250 ml of tetrahydrofuran (THF) in the round flask, and agitated for 30 min, and 10 ml of 1,4-dibromobutane (Sigma-Aldrich, Co., Ltd., purity 99%) was slowly applied in drops by using the dropping funnel. After the application was finished, the temperature was increased to 50° C. to perform the reaction. After finishing of the reaction was confirmed by GC, the organic layer was washed with water by using the separatory funnel, the solvent was vaporized, and the product having purity of 95.0% was obtained through distillation of the reaction product. $^1$H-NMR(CDCl$_3$, 500 MHz) : δ 1.37(18H,d), 1.59 (6H,m), 3.38 (6H,s), 3.40~3.68(20H,m)

EXAMPLE 13

Manufacturing of the Resin Composition

The polycarbonate sheet was manufactured in order to evaluate performance of the plasticizer manufactured in Examples 1 to 12. The sample of the polycarbonate sheet was manufactured by putting 100 parts by weight of the polypropylene carbonate resin having the molecular weight of 200,000 g/mol and 20 parts by weight of the plasticizer into the mixer, mixing them, and performing works of preheating at 140° C. for 1 min, pressing for 1.5 min, and cooling for 1.5 min by using the press machine to manufacture the sheet having the thickness of 0.5 mm.

COMPARATIVE EXAMPLE 1

The sample was manufactured by the same method as Example 13 without using the plasticizer. The same test as that performed in Example 13 was performed by the manufactured sample, and the results are arranged in the following Table 2.

TABLE 2

| | Evaluation of physical properties | | | | | |
|---|---|---|---|---|---|---|
| Classification | Hardness, (Shore A) | Tensile strength, (Kgf/cm$^2$) | Elongation (%) | Modulus, (Kgf/cm$^2$) | Bleeding | Tg (° C.) |
| Example 1 | 39 | 122 | 483 | 30 | No | −4.1 |
| Example 2 | 39 | 122 | 470 | 30 | No | −1.2 |
| Example 3 | 42 | 124 | 461 | 32 | No | −3.5 |
| Example 4 | 40 | 123 | 457 | 33 | No | −3.0 |
| Example 5 | 46 | 126 | 435 | 35 | No | 0.8 |
| Example 6 | 48 | 130 | 405 | 38 | No | −2.5 |
| Example 7 | 37 | 118 | 495 | 28 | No | −11.9 |
| Example 8 | 37 | 120 | 490 | 29 | No | −11.4 |
| Example 9 | 39 | 121 | 487 | 30 | No | −10.0 |
| Example 10 | 38 | 118 | 492 | 27 | No | −11.7 |
| Example 11 | 44 | 126 | 434 | 33 | No | 12.2 |
| Example 12 | 48 | 130 | 412 | 36 | No | 20.8 |
| Comparative Example 1 | 56 | 123 | 386 | 39 | No | 33.3 |

As shown in Table 1, it can be confirmed that the resin composition including the plasticizer according to the present invention of Examples 1 to 12 has excellent plasticizing efficiency, hardness, tensile strength, elongation and modulus and bleeding does not occur to significantly improve compatibility with the resin. Further, shaping into the film is excellent because the glass transition temperature is low, it is possible to perform various shaping according to various purposes because flexibility is maintained at low temperatures, and a life-span of products can be extended because extraction property by an organic solvent or water is low.

Although the present invention has been described in detail in connection with the exemplary embodiments of the present invention, it will be apparent to those skilled in the art that various modifications and changes may be made thereto without departing from the scope and spirit of the invention defined in the accompanying claims. Therefore, it should be understood that the present invention is not limited to the aforementioned embodiments.

The invention claimed is:

1. A resin composition comprising:
   a polyalkylene carbonate resin; and
   a plasticizer represented by the following Formula 4:

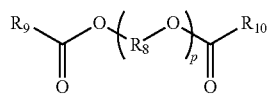

[Formula 4]

wherein,
$R_8$ is straight- or side-chained C1-C8 alkylene, C5-C10 cycloaliphatic alkylene or C6-C12 arylene, $R_9$ and $R_{10}$ are each independently a straight- or side-chained C1-C18 alkyl group, a C5-C10 cycloaliphatic alkyl group or a C6-C12 aryl group, and p is 1 to 40, and the resin composition has an elongation of 405% to 495%.

2. The resin composition of claim 1, wherein $R_8$ is ethylene or propylene, $R_9$ and $R_{10}$ are each independently a methyl or acetyl, and p is 4 to 8.

3. The resin composition of claim 1, wherein the resin composition includes 1 to 70 parts by weight of the plasticizer based on 100 parts by weight of the resin.

4. The resin composition of claim 1, wherein the polyalkylene carbonate is polypropylene carbonate or polyethylene carbonate.

5. The resin composition of claim 1, wherein the weight average molecular weight of polyalkylene carbonate resin is 2,000 to 3,000,000 g/mol.

6. The resin composition of claim 1, wherein the specific gravity of the polyalkylene carbonate resin is 1.0 to 1.3.

* * * * *